| United States Patent [19] | [11] | 4,044,000 |
| --- | --- | --- |
| Koppel | [45] | Aug. 23, 1977 |

[54] SUBSTITUTED β-LACTAM ANTIBIOTICS

[75] Inventor: Gary A. Koppel, Indianapolis, Ind.

[73] Assignee: Eli Lilly and Company, Indianapolis, Ind.

[21] Appl. No.: 716,606

[22] Filed: Aug. 23, 1976

Related U.S. Application Data

[60] Division of Ser. No. 545,451, Jan. 30, 1975, Pat. No. 3,994,885, which is a division of Ser. No. 301,694, Oct. 27, 1972, abandoned, Continuation-in-part of Ser. No. 222,293, Jan. 31, 1972, abandoned.

[51] Int. Cl.$^2$ .............. C07D 499/44; C07D 499/46; C07D 499/50; C07D 499/58
[52] U.S. Cl. ................................. 260/239.1; 424/271
[58] Field of Search ........................ 260/239.1, 243 C

[56] References Cited

U.S. PATENT DOCUMENTS

| 3,775,410 | 11/1973 | Christensen et al. | 260/243 C |
| 3,778,432 | 12/1973 | Pines | 260/243 C |
| 3,780,031 | 12/1973 | Christensen et al. | 260/243 C |
| 3,780,034 | 12/1973 | Christensen et al. | 260/243 C |
| 3,780,037 | 12/1973 | Hazen | 260/243 C |

OTHER PUBLICATIONS

J.A.C.S. vol. 93, No. 9, pp. 2308-2312 (5-5-71).

*Primary Examiner*—Gerald A. Schwartz
*Attorney, Agent, or Firm*—William B. Scanlon; Everet F. Smith

[57] ABSTRACT

6-Alkoxylated-6-acylamidopenicillanic acids and 7-alkoxylated-7-acylamidocephalosporin acids and esters thereof, are provided by reacting a 6-acylamidopenicillanic acid ester or a 7-acylamidocephalosporin ester under anhydrous conditions at −90° C. to −15° C. with an alkali metal salt of a lower alkyl alcohol in the presence of an excess of the corresponding alcohol to produce, in situ, the anionic form of the antibiotic which on halogenation with a positive halogen compound, e.g. t-butyl hypochlorite, yields the compound of the invention. Compounds of the invention, e.g. 6-methoxy-6-phenoxy-acetamidopenicillanic acid and 7-methoxy-7-[2-(2-thienyl)acetamido]cephalosporanic acid are useful antibiotics.

3 Claims, No Drawings

SUBSTITUTED β-LACTAM ANTIBIOTICS

This is a division of application Ser. No. 545,451 filed Jan. 30, 1975, now U.S. Pat. No. 3,994,885, which was a division of application Ser. No. 301,694 filed Oct. 27, 1972 as a continuation-in-part of application Ser. No. 222,293 filed Jan. 31, 1972, both now abandoned.

BACKGROUND OF THE INVENTION

This invention relates to the β-lactam antibiotics, the penicillins and the cephalosporins. In particular, this invention relates to 6-alkoxylated 6-acylaminodopenicillanic acids and 7-alkoxylated 7-acylamidocephalosporins and to a process for the preparation thereof.

Numerous penicillin and cephalosporin antibiotics have been prepared by semi-synthetic means. For example, the nucleus of penicillin, 6-aminopenicillanic acid (6-APA), has been acylated with a wide variety of acylating agents to obtain active penicillin antibiotics. Likewise, the cephalosporin nucleus, 7-aminocephalosporanic acid (7-ACA), has been derivatized in like manner to provide a wide variety of biologically active 7-acylamidocephalosporanic acids. Further, the semi-synthetic nucleus of the cephalosporin antibiotics, 7-aminodeacetoxycephalosporanic acid (7-ADCA), has been acylated with a wide variety of acyl moieties to provide active 7-acylamidodeacetoxycephalosporanic acids. More recently, the cephalosporin nucleus which bears a 3-acetoxymethyl substituent has been further derivatized by the replacement of the acetoxy group with a wide variety of substituents.

Heretofore, cephalosporins and penicillins bearing a substituent on a carbon of the β-lactam ring have been little described in the literature.

7-Methoxycephalosporin C and 7-(5-amino-5-carboxyvaleramido)-7-methoxy-3-carbamoyloxymethyl-3-cephem-4-carboxylic acid obtained from the fermentation of *Streptomyces lipmanii* and *Streptomyces clavuligerus* are described in *J. Am. Chem. Soc.* 93, 2308 (1971). 6-Methylpenicillin has been suggested by Strominger, *Amer. J. Med.*, 39, 708 (1965).

It is an object of this invention to provide novel derivatives of cephalosporin and penicillin antibiotics. It is a further object of this invention to provide 6-alkoxy-6-acylamido penicillanic acids and 7-alkoxy-7-acylamidocephalosporanic acids and deacetoxycephalosporanic acids. It is also an object of this invention to provide a process for the preparation of substituted cephalosporins and penicillins wherein the substituent group is introduced into the 6- and 7-positions of the penicillin and cephalosporin nuclei, respectively.

SUMMARY OF THE INVENTION

The compounds provided by this invention are represented by the following general formula,

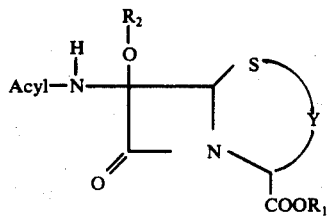

wherein the term "acyl" represents a wide variety of known side chains of the cephalosporin and penicillin antibiotics such as phenylacetyl, phenylthioacetyl, 2-thiopheneacetyl, phenylglycyl, mandelyl, and the like; $R_1$ represents hydrogen, an alkali metal cation, acetoxymethyl or an ester-forming moiety and preferably one which is readily removed so as to provide the carboxylic acid form of the desired antibiotic; and wherein $R_2$ represents $C_1$–$C_4$ lower alkyl, allyl, propargyl, $C_3$–$C_6$ cycloalkyl or benzyl; Y is the remaining carbon fragment of the dihydrothiazine ring of the cephalosporin or the remaining carbon fragment of the thiazolidine ring of the penicillin.

As used herein, the term, "cephalosporin," refers to those compounds having the 3-cephem ring structure and includes 3-methyl-3-cephem compounds, the deacetoxycephalosporanic acids, and the 3-acetoxymethyl-3-cephem compounds, the cephalosporanic acids. The term, "cephalosporanic acid," has reference to the 3-acetoxymethyl-3-cephem antibiotics.

The compounds of the above general formula are prepared by reacting a penicillanic acid or a cephalosporin acid, an alkali metal salt or an ester thereof and preferably an ester which is readily removed to provide the free carboxylic acid such as the benzyl ester, benzhydryl ester or the trichloroethyl ester, in an inert solvent at sub-zero temperatures and preferably between about −90° C. and −15° C. with an alkali metal alkoxide, cycloalkoxide or benzyloxide, in the presence of an excess of the alcohol corresponding to the alkoxide. To the cold reaction mixture is then added a positive halogen compound such as, for example, tertiary-butyl hypochlorite or N-chloroacetamide and the reaction mixture stirred in the cold for an additional 5 to 20 minutes. Thereafter the reaction is quenched by the addition of glacial acetic acid or formic acid. The alkoxylated penicillins and cephalosporins can be recovered from the reaction mixture by conventional isolation procedures to provide the 6- or 7-substituted penicillin or cephalosporin ester. Removal of the ester group provides a compound of the invention represented by the above formula wherein $R_1$ is hydrogen.

The compounds of the invention exhibit the usual infrared absorption characteristics exhibited by the unsubstituted penicillanic acids and cephalosporanic acids. The compounds of the invention also exhibit the characteristic ultraviolet spectra of the penicillanic acids and cephalosporanic acids.

The 6-substituted penicillins and 7-substituted cephalosporins provided by this invention exhibit both gram positive and gram negative microbiological activity.

DETAILED DESCRIPTION OF THE INVENTION

The novel substituted penicillins and cephalosporins provided by this invention, previously described in general, are represented by the following Formula I.

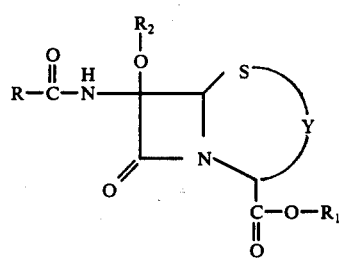

wherein R is hydrogen, $C_1$-$C_6$ alkyl, 4-amino-4-carboxybutyl, phenyl, substituted phenyl or a group of the formula

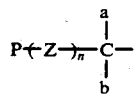

wherein
P is phenyl, lower alkylphenyl, halophenyl, hydroxyphenyl, lower alkoxyphenyl,
2-thienyl, 3-thienyl, 2-furyl, 3-furyl or 1-tetrazyl;
Z is an oxygen atom, or a sulfur atom;
n is 0 and 1;
a is hydrogen or $C_1$-$C_3$ lower alkyl,
b is hydrogen, $C_1$-$C_3$ lower alkyl, hydroxy, protected hydroxy, amino or protected amino; and when n is 1, P is phenyl, $C_1$-$C_4$ lower alkylphenyl, halophenyl, hydroxyphenyl, $C_1$-$C_4$ lower alkoxyphenyl and b is hydrogen or $C_1$-$C_3$ lower alkyl;
$R_1$ is hydrogen, an alkali metal cation, acetoxymethyl or a readily removable ester forming moiety;
$R_2$ is $C_1$-$C_4$ lower alkyl, allyl, propargyl, $C_3$-$C_6$ cycloalkyl or benzyl;
Y is a 3-carbon fragment of the formula

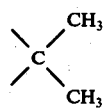

or a substituted 3-carbon fragment of the formula

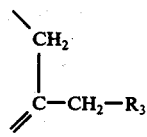

wherein
$R_3$ is hydrogen, $C_2$-$C_4$ alkanoyloxy, $C_1$-$C_4$ alkoxy $C_1$-$C_4$ alkylthio, or pyridinium,

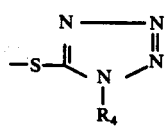

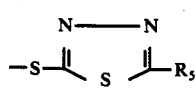

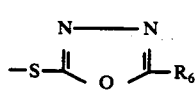

wherein $R_4$, $R_5$ and $R_6$ are hydrogen, $C_1$-$C_4$ lower alkyl, phenyl, $C_1$-$C_4$ lower alkylphenyl, halophenyl, hydroxyphenyl or $C_1$-$C_4$ lower alkoxyphenyl; or a carbamoyloxy group of the formula

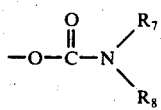

wherein $R_7$ and $R_8$ can be the same or different
and are hydrogen or $C_1$-$C_4$ lower alkyl; subject to the limitation that when $R_3$ is $C_2$ alkanoyloxy or a carbamoyloxy group wherein $R_7$ and $R_8$ are both hydrogen or when Y is the 3-carbon fragment

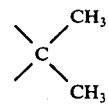

then $R_2$ is $C_2$-$C_4$ alkyl, allyl, propargyl, $C_3$-$C_6$ cycloalkyl or benzyl.

The term, "substituted phenyl," has reference herein to phenyl substituted by one or more substituent groups selected from among chloro, bromo, fluoro, $C_1$-$C_4$ lower alkyl, for example methyl, ethyl and isopropyl, hydroxy, nitro, amino, aminomethyl, $C_1$-$C_4$ lower alkoxy, for example, methoxy, ethoxy and isopropoxy, and carboxy. Such substituted phenyl radicals represented by R can be for example, 4-hydroxyphenyl, 3,4-dichlorophenyl, 2,6-dimethoxyphenyl, 4-methylphenyl, 4-carboxyphenyl, 3- or 4-nitrophenyl, p-aminophenyl, m-aminophenyl, 4-aminomethylphenyl and 4-ethoxyphenyl.

The term, "$C_3$-$C_6$ cycloalkyl," refers to cyclopropyl, cyclobutyl, cyclopentyl and cyclohexyl.

The term, "$C_1$-$C_4$ alkylthio," refers to methylthio, ethylthio, n-propylthio, isopropylthio, n-butylthio and like groups.

The term, "$C_1$-$C_6$ alkyl" as used herein refers to methyl, ethyl, n-propyl, iso-propyl, n-butyl, iso-butyl, t-butyl, n-amyl, iso-amyl, n-hexyl and like aliphatic hydrocarbon radicals. "Lower alkyl" refers to the $C_1$-$C_4$ straight and branched chain hydrocarbon radicals such as methyl, ethyl, n-propyl, iso-propyl, n-butyl, sec-butyl, and t-butyl. Likewise, the term, "$C_1$-$C_3$ lower alkyl" has reference to the aliphatic hydrocarbon radicals containing from 1 to 3 carbon atoms. The term, "halophenyl" has reference to mono and dichlorophenyl, mono- and dibromophenyl or mono- and difluorophenyl. "Lower alkyl phenyl" refers to the mono- and dialkyl substituted phenyl groups such as methylphenyl, ethylphenyl, n-propylphenyl, iso-propylphenyl, dimethylphenyl, methylethylphenyl and the like. The term, "hydroxyphenyl", refers to the mono- or dihydroxy-substituted phenyl group such as p-hydroxyphenyl, m-hydroxyphenyl, 3,4-dihydroxyphenyl and the like. "Lower alkoxyphenyl" refers to the mono- and di-substituted alkyl phenyl ethers such as methoxyphenyl, ethoxyphenyl, n-propoxyphenyl, 2,6-dimethoxyphenyl and the like.

The term "protected amino" as employed herein refers to the amino group substituted by one of the commonly employed protecting groups, for example, t-butyloxycarbonyl, 2,2,2-trichloroethoxycarbonyl, benzyloxycarbonyl, and like protecting groups. "Protected hydroxy" refers to an hydroxyl group substituted by any of the commonly employed hydroxyl protecting groups such as benzyl, benzhydryl, t-butyloxycarbonyl (t-BOC), benzyloxycarbonyl, 2,2,2-trichloroethoxycarbonyl, and ethylvinyl ether. It is preferable to employ an hydroxyl protecting group, such as one of those mentioned above, which is substantially stable under the basic conditions used in the present process for the preparation of the penicillin and cephalosporin anionic forms. Any protecting group which is stable under the conditions of temperature and pH of the process can be used, and the particular protecting group chosen is not critical in the present process.

The term, "a readily removable ester forming moiety," has reference to the commonly employed carboxylic acid protecting groups employed for protecting the $C_4$ carboxylic acid group of the cephalosporins and the $C_3$ carboxylic acid group of the penicillins. Representative of such groups are t-butyl, benzyl, benzhydryl, p-nitrobenzyl, 4-methoxybenzyl, 2,2,2-trichloroethyl, phenacyl, 3,5-dimethoxybenzyl or tetrahydropyranyl and like cleavable ester moieties.

Illustrative of the 7-acyl groups represented by the structural moiety,

of the formula 1 are formyl, acetyl, propionyl, benzoyl, 2,6-dimethoxybenzoyl, 4-hydroxybenzoyl, 3-bromobenzoyl, 4-nitrobenzoyl, 4-aminobenzoyl, 3-aminobenzoyl, phenylacetyl, 4-hydroxyphenylacetyl, 4-methoxyphenylacetyl, 4-methyl-phenylacetyl, phenoxyacetyl, 4-hydroxyphenylacetyl, 3,4-dichlorophenoxyacetyl, 3-methylphenoxyacetyl, phenyl-thioacetyl, 4-chlorophenylthioacetyl, 4-methylphenylthioacetyl, 3-bromophenylthioacetyl, mandeloyl, 4-hydroxymandeloyl, phenylglycyl, 4-methylphenylglycyl, 4-hydroxyphenylglycyl, 3-methoxyphenylglycyl, 2-thienylacetyl, 3-thienylacetyl, 2-furylacetyl, 5-methyl-1-tetrazylacetyl and the like.

Illustrative of the radicals represented by $R_3$ are methoxy, ethoxy, methylthio, n-propylthio, acetoxy, propionoxy, pyridinium, 1-methyl-1H-tetrazol-5-ylthio, 1-phenyl-1H-tetrazol-5-ylthio, 1-p-chlorophenyl-1H-tetrazol-5-ylthio; 5-methyl-1,3,4-thiadiazol-2-ylthio; 5-phenyl-1,3,4-thiadiazole-2-ylthio; 5-methyl-1,3,4-oxadiazol-2-ylthio, 5-phenyl-1,3,4-oxadiazol-2-ylthio, carbamoyloxy, N-methylcarbamoyloxy, N,N-dimethylcarbamoyloxy, N,N-diethylcarbamoyloxy, N-butylcarbamoyloxy and N-methyl-N-ethylcarbamoyloxy.

The following compounds are illustrative of the 7-substituted 7-acylamido cephalosporin compounds provided by the present invention.
7-acetamido-7-methoxy-3-methyl-3-cephem-4-carboxylic acid,
7-methoxy-3-methyl-7-(2-phenylacetamido)-3-cephem-4-carboxylic acid,
7-ethoxy-7-(2-phenoxyacetamido)cephalosporanic acid,
7-formamido-7-methoxy-3-methyl-3-cephem-4-carboxylic acid,
7-allyloxy-3-methyl-7-(2-phenylacetamido-3-cephem-4-carboxylic acid,
7-isopropoxy-7-[2(2-thienyl)acetamido]cephalosporanic acid,
7-methoxy-3-methyl-7-[2-(2-thienyl)acetamido]-3-cephem-4-carboxylic acid,
7-n-butoxy-7-(2-phenylacetamido)cephalosporanic acid,
7-methoxy-3-methyl-7-(2-phenylthioacetamido)-3-cephem-4-carboxylic acid,
7-[2-(m-hydroxyphenyl)acetamido]7-isopropoxy-3-methyl-3-cephem-4-carboxylic acid,
7-(5-amino-5-carboxyvaleramido)-7-ethoxycephalosporanic acid,
7-(5-amino-5-carboxyvaleramido)-7-benzyloxycephalosporanic acid,
7-ethoxy-3-methyl-7-[2-(3-thienyl)acetamido]-3-cephem-4-carboxylic acid,
7-[2-(2-furyl)acetamido]-7-isopropoxycephalosporanic acid,
7-n-butoxy-7-[2-(4-chlorophenyl)acetamido]-3-methyl-3-cephem-4-carboxylic acid,
7-methoxy-3-methoxymethyl-7-(2-phenylacetamido)-3-cephem-4-carboxylic acid,
7-methoxy-3-methylthiomethyl-7-(2-phenoxyacetamido)-3-cephem-4-carboxylic acid,
3-carbamoyloxymethyl-7-n-propoxy-7-[2-(2-thienyl)acetamido]-cephem 4-carboxylic acid,
7-n-butoxy-7-n-butyramido-3-methoxymethyl-3-cephem-4-carboxylic acid,
7-benzamido-7-methoxy-3-(N-methylcarbamoyloxymethyl)-3-cephem-4-carboxylic acid,
7-(2-amino-2-phenylacetamido)-7-methoxy-3-methyl-3-cephem-4-carboxylic acid,
7-(2-t-butoxycarbonylamino-2-phenylacetamido)-7-ethoxy-3-methyl-3-cephem-4-carboxylic acid;
7-mandelamido-7-methoxy-3-methyl-3-cephem-4-carboxylic acid,
7-(2-benzhydryloxy-2-phenylacetamido-7-methoxy-3-methyl-3-cephem-4-carboxylic acid,
7[2-amino-2-(p-hydroxyphenyl)acetamido]-7-methoxy-3-methyl-3-cephem-4-carboxylic acid,
7-cyclopropoxy-3-methyl-7-(2-phenylacetamido)-3-cephem-4-carboxylic acid,
7-cyclopropoxy-3-methyl-7-(2-phenoxyacetamido)-3-cephem-4-carboxylic acid,
7-(2-amino-2-phenylacetamido)-7-cyclopentoxy-3-ethoxymethyl-3-cephem-4-carboxylic acid,
7-(2-phenylacetamido)-7-propargloxycephalosporanic acid,
7-isopropoxy-3-propionyloxymethyl-7-[2-(2-thienyl)acetamido]3-cephem-4-carboxylic acid,
7-[2-amino-2-(3-thienyl)acetamido]-7-methoxy-3-methyl-3-cephem-4-carboxylic acid,
7-[2-(2,6-dimethoxyphenyl)acetamido]-7-methoxy-3-methyl-3-cephem-4-carboxylic acid,
7-[2-(p-bromophenyl)acetamido]-3-carbamoyloxymethyl-7-isopropoxy-3-cephem-4-carboxylic acid,
7-[2-(3,4-dimethoxyphenyl)acetamido]-3-isopropoxymethyl-7-ethoxy-3-cephem-4-carboxylic acid,
7-(5-amino-5-carboxyvaleramido)-7-methoxy-3-methyl-3-cephem-4-carboxylic acid,
7-methoxy-3-(5-methyl-1,3,4-oxadiazol-2-ylthiomethyl)-7-[2-(2-thienyl)acetamido]-3-cephem-4-carboxylic acid,
7-cyclopropoxy-3-(1-methyl-IH-tetrazol-5-ylthiomethyl)-7-(2-phenoxyacetamido)-3-cephem-4-carboxylic acid,
7-ethoxy-3-(5-methyl-1,3,4-thiadiazol-2-ylthiomethyl)-7-(2-hydroxy-2-phenylacetamido)-3-cephem-4-carboxylic acid,
7-allyloxy-3-(1,3,4-thiadiazol-2-ylthiomethyl)-7-(2-phenylacetamido)-3-cephem-4-carboxylic acid,
7-methoxy-7-[2-(1-tetrazyl)acetamido]-3-methoxymethyl-3-cephem-4-carboxylic acid,
7-methoxy-7-[2-(1-tetrazyl)acetamido]-3-methylthiomethyl-3-cephem-4-carboxylic acid, 7-methoxy-3-(5-phenyl-1,3,4-thiadiazol-2-ylthiomethyl)-7-[2-(2-thienyl)acetamido]-3-cephem-4-carboxylic acid, 7-methoxy-3-[1-(4-chlorophenyl)-IH-tetrazol-5-ylthiomethyl]-7-[2-amino-2-(4-hydroxyphenyl)acetamido]-3-cephem-4-carboxylic acid, and the like.

7-methoxy-7-mandelamido-3-(N,N-dimethylcarbamoyloxymethyl)-3-cephem-4-carboxylic acid, 7-methoxy-7-[2-(2-thienyl)acetamido]-3-(N-methyl-carbamoyloxymethyl)-3-cephem-4-carboxylic acid, and the like.

The following 6-substituted 6-acylamidopenicillanic acids are representative of those provided by the present invention:

6-(2,6-dimethoxybenzamido)-6-ethoxypenicillanic acid,
6-(2-phenylacetamido-6-propoxypenicillanic acid,
6-allyloxy-6-butyramidopenicillanic acid,
6-(2-phenylacetamido-6-propargyloxypenicillanic acid,
6-cyclopropoxy-6-(2-phenylacetamido)penicillanic acid,
6-cyclohexyloxy-6-(2-phenoxyacetamido)penicillanic acid,
6-[2-(3,4-dichlorophenyl)acetamido]-6-isopropoxypenicillanic acid,
6-ethoxy-6-[2-(p-ethoxyphenyl)acetamido]penicillanic acid,
6-(2-methyl-2-phenylacetamido)-6-n-propoxypenicillanic acid,
6-benzyloxy-6-[2-(2-thienyl)acetamido penicillanic acid,
6-(2-amino-2-phenylacetamido)-6-methoxypenicillanic acid,
6-cyclopropoxy-6-(2-phenylthioacetamido)penicillanic acid,
6-[2-(p-bromophenoxy)acetamido]-6-n-butoxypenicillanic acid and the like.

Preferred compounds of the present invention are those represented by the Formula I wherein $R_2$ is methyl. An especially preferred group of compounds provided by this invention are those compounds represented by the formula I wherein $R_2$ is methyl, Y is the substituted 3-carbon fragment

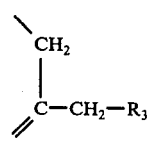

wherein $R_3$ is

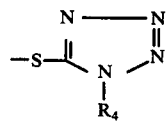

and $R_4$ is other than hydrogen. These especially preferred compounds are represented by the formula.

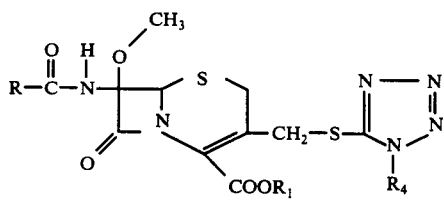

wherein $R_4$ is other than hydrogen. Illustrative compounds represented thereby are 7-methoxy-7-[2-(1-tetrazyl)acetamido]-3-(1-methyl-1H-tetrazole-5-ylthiomethyl)-3-cephem-4-carboxylic acid, 7-methoxy-7-mandelamido-3-(1-methyl-1H-tetrazole-5-ylthiomethyl)-3-cephem-4-carboxylic acid, and 7-methoxy-7-[2-(2-thienyl)acetamido]-3-(1-methyl-1H-tetrazol-5-ylthiomethyl)-3-cephem-4-carboxylic acid, and the acetoxymethyl esters and alkali metal salts thereof.

As is the case with non-alkoxylated penicillanic acids and cephalosporanic acids the compounds of this invention readily form salts such as the lithium, sodium, and potassium salts by the reaction of the free antibiotic acid in a suitable solvent with an alkali metal carbonate or bicarbonate.

The compounds represented by the Formula I, wherein $R_1$ is acetoxymethyl, are ester derivatives of the penicillanic and cephalosporin free acids which possess the antibiotic activity of the free acid forms of the antibiotics and are relatively stable esters. In contrast, the readily removable esters represented when $R_1$ is a readily removable ester forming moiety, for example the p-nitrobenzyl or 2,2,2-trichloroethyl esters, are themselves substantially inactive antibiotic compounds. However, such esters are useful intermediates in the preparation of the antibiotic free acids in the process of the invention as described hereinafter.

According to another aspect of the present invention, a novel process is provided for the preparation of the compounds represented by the Formula I. According to this invention, a 6-acylamidopenicillanic acid ester or a 7-acylamidocephalosporin ester represented by the Formula II

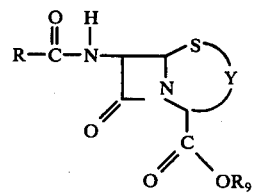

wherein R, and Y have the same meanings as defined in Formula I except that when Y is a substituted 3-carbon fragment of the formula

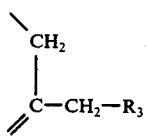

$R_3$ is hydrogen, $C_2$-$C_4$ alkanoyloxy, $C_1$-$C_4$ alkoxy, $C_1$-$C_4$ alkylthio;

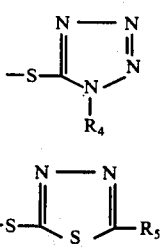

-continued

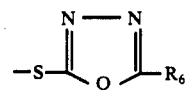

or a carbamoyloxy group of the formula

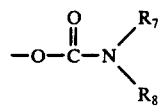

wherein $R_4$, $R_5$, $R_6$, $R_7$ and $R_8$ have the same meanings as defined in Formula I; and $R_9$ is acetoxymethyl or a readily removable ester forming group; is reacted in an inert, anhydrous, solvent with an alkali metal salt of a $C_1$-$C_4$ alkyl carbinol, allyl alcohol, propargyl alcohol, a $C_3$-$C_6$ cycloalkyl carbinol, or benzyl alcohol, represented by the formula $$M^+ OR_2^-$$

wherein $R_2$ is $C_1$-$C_4$ lower alkyl, $C_3$-$C_6$ cycloalkyl, allyl, propargyl or benzyl and $M^+$ is an alkali metal cation, in the presence of an excess amount of the corresponding alcohol, $HOR_2$, at a temperature between about $-95°$ C. and about $-15°$ C. to provide the anionic form of the compound of Formula II. To the reaction solution of the anionic form is added a halogenating agent which under the conditions of the reaction is capable of supplying positive halogen. The reaction mixture is allowed to stir at the reaction temperature for about 5 to 15 minutes and is thereafter quenched with a carboxylic acid such as formic acid or glacial acetic acid to provide a reaction product mixture containing the 6-substituted penicillanic acid ester or the 7-substituted cephalosporin ester. The reaction mixture is evaporated in vacuo to dryness and the residue is dissolved in a suitable organic solvent. The solution is then washed with a weak base such as sodium bicarbonate and then dried and the dried solution evaporated to yield the crude reaction product mixture containing the desired product. The product is purified by recrystallization or perferably by chromotagraphy over silica.

Alkali metal salts of the alcohols which can be employed in the present process include for example lithium methoxide, potassium methoxide, sodium methoxide, lithium ethoxide, lithium allyloxide, lithium cyclopropoxide, lithium propargyloxide, the lithium, sodium and potassium salts of benzyl alcohol and the like.

In general, the alkali metal salts of the alcohols are prepared in situ in the presence of an excess amount of the corresponding alcohol in the inert, dry solvent, and the starting penicillanic acid ester or cephalosporin ester is added thereto to generate the anion. The amount of the alkali metal salt which can be employed in the present process is between about 2 and 6 equivalents per 1 equivalent of the penicillin or the cephalosporin employed. The preferred amount is about 3.5 equivalents of alkali metal salt to one equivalent of the antibiotic.

Inert solvents which are suitable in the present process include tetrahydrofuran, dioxane, dimethylformamide, dimethylacetamide, the dimethylether of ethylene glycol, and polyethers such as diethylene glycol dimethyl ether. The particular solvent employed in the present process is unimportant and any suitable inert solvent can be employed. However, it is a requirement of the present process that the solvent employed to anhydrous since minor amounts of water drastically reduce the yield of the desired product.

As previously mentioned the reaction of an alkali metal salt of an alcohol, $M^+ OR_2^-$, with the antibiotic ester is carried out in the presence of an excess of the corresponding alcohol. By an excess amount is meant an amount greater than 1 equivalent of the antibiotic employed and generally an excess between 10 and 30 equivalents can be used since such excess is not critical in the process.

The halogenating agents which can be employed in the present process are those which are generally recognized as positive halogen sources. The term, "positive halogen source," refers to any halogen compound capable of supplying a positive halogen atom, for example, $Cl^+$, $Br^+$ and $I^+$. A wide variety of such compounds are known and recognized as sources of positive halogens. For example, chlorine, bromine, N-haloamides and N-haloimides such as N-chlorosuccinimide, N-bromosuccinimide, N-chloroacetamide, the N-halosulfonamides such as N-chloro-benzenesulfonamide and N-chloro-p-toluenesulfonamide, the 1-halobenzotriazoles such as 1-bromobenzotriazole, also the halotriazines, the organic hypochlorites such as t-butyl hypochlorite and t-butyl hypoiodide, the halohydantoins, such as N,N-dibromohydantoin can be employed as positive halogen sources. A preferred halogenating agent, acting as a source of positive chlorine in the present process, is t-butyl hypochlorite.

The halogenating agent is desirably used in an amount sufficient to provide 1 equivalent of positive halogen per equivalent of the antibiotic employed in the reaction.

The entire process is carried out over a relatively short period of time. For example, upon the addition of the cephalosporanic acid ester or the penicillanic acid ester to a solution of the alkali metal salt of the alcohol in an inert solvent, the anion is generated rapidly and thereafter the halogenating agent can be added to the reaction mixture almost immediately. The reaction mixture is maintained in the cold between about 5 and 20 minutes and is thereafter quenched by acidification.

Suitable acids which can be employed in the acidification are those which when added to the cold reaction mixture do not cause freezing of the reaction mixture into a solid or heavy viscous mixture. Suitable acids are the low molecular weight alkyl carboxylic acids such as formic acid, acetic acid, or propionic acid, the chlorinated alkyl carboxylic acids such as trichlorocetic acid, and the lower alkylsulfonic acids such as methanesulfonic acid. Aqueous mineral acids are undesirable due to the high content of water which rapidly freezes in the cold reaction mixture. Glacial acetic acid and 98% formic acid are the preferred acids in the present process.

The reaction is usually carried out by first preparing a solution of the alkali metal salt of the desired alcohol in an excess of the corresponding alcohol in an inert anhydrous, solvent such as tetrahydrofuran and cooling the mixture to the reaction temperature. Thereafter, a solution of the desired penicillin or cephalosporin compound in anhydrous tetrahydrofuran is added rapidly by dropwise addition to the reaction vessel. The reaction mixture is stirred for a short time, and generally only about 3 minutes is required to generate the anionic form, and thereafter the halogenating agent is added rapidly to the solution of the antibiotic anion. The reaction mixture is then stirred for an additional 5 or 10 minutes at the reaction temperature and is thereafter quenched by the addition of an excess amount of formic acid or acetic acid. The reaction can be carried out, however, over longer periods of time provided the temperature is maintained at the reaction temperature.

Following treatment of the reaction mixture with formic acid or glacial acetic acid, the reaction mixture is evaporated to dryness and the residue is dissolved in a suitable solvent such as a halogenated hydrocarbon, for example, dichloromethane, chloroform, or carbon tetrachloride, or an ester such as ethyl acetate or amyl acetate or other suitable solvent. This solution is washed with a saturated solution of sodium thiosulfate to remove excess halogen, and then with a saturated solution of sodium bicarbonate to remove any residual acid which may be present. The washed solution is then dried and thereafter is evaporated to dryness in vacuo to yield the reaction product mixture which occasionally contains some unreacted starting material. The substituted antiobiotic and the starting material can be conveniently separated from each other by chromatography. Suitable chromatographic materials which can be employed in the separation of the alkoxylated antiobiotic from its starting material are silica gel and alumina. Likewise, when the reaction is carried out on a small scale, the reaction product can be isolated by means of preparative thin layer chromatography.

The foregoing process is conveniently illustrated by the following reaction scheme.

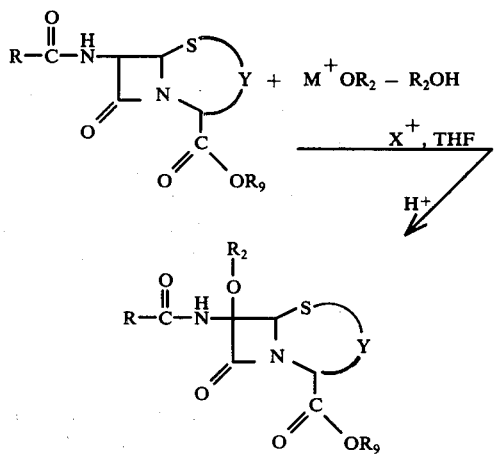

wherein R, $R_2$, $R_9$, and Y have the same meanings as previously defined and M = Li, Na, K, and THF = tetrahydrofuran.

The preferred conditions and reagents of the above-described process are as follows.

It is preferred to employ an ester of a 6-acylamidopenicillanic acid or a 7-acylamidocephalosporin as the starting material in the present invention, a particularly useful ester being the 2,2,2-trichloroethyl ester.

Although the free carboxylic acid form of the starting penicillin or cephalosporin can be used, yields of the reaction products are higher than when an ester is employed.

Tetrahydrofuran is the preferred solvent, t-butyl hypochlorite is the preferred halogenating agent and the reaction is carried out preferably at about $-80°$ C. When the reaction is carried out in the preferred manner and with the preferred reagents, yields of the substituted antibiotics on the order of between about 40 and 95 percent are commonly obtained.

The alkoxylated $\beta$-lactam compounds provided by this invention have spectral properties analogous to those of the non-alkoxylated penicillins and cephalosporins. For example, the presence of the $\beta$-lactam ring carbonyl is shown in the products by the presence of an absorption maximum in the infrared at approximately 1790 $cm^{-1}$. The compounds of this invention likewise exhibit the characteristic ultraviolet absorption spectra of the unsubstituted penicillins and cephalosporins. The nuclear magnetic resonance spectra of the compounds of the invention, as expected, show the absence of the peaks attributable to the hydrogens attached to the adjacent carbon atoms of the $\beta$-lactam ring, for example, in the penicillins, the hydrogens attached to $C_5$ and $C_6$, and in the cephalosporins the adjacent hydrogens attached at $C_6$ and $C_7$. Instead, the spectra of the compounds of the invention show only a singlet for the remaining proton attached to the carbon of the ring juncture resulting from the $C_5$ proton of the penicillin and the $C_6$ proton of the cephalosporin.

When in Formula I, R is 4-amino-4-carboxybutyl, it is preferable to protect the free amino group of the side chain (aminoadipoyl) during the substitution reaction of the present process. Commonly employed amino protecting groups can be used in the present process, for example, t-butyloxycarbonyl, benzyloxycarbonyl, 2,2,2-trichloroethoxycarbonyl and like amino protecting groups can be employed. Likewise, when R in the Formula I is 2-hydroxy-2-phenylacetamido, the mandelic acid side chain, the hydroxy group is protected during the substitution reaction of the present invention. The hydroxy group can be conveniently protected by such groups as benzyl, benzhydryl, tetrahydropyranyl, ethyl vinyl ether and like hydroxyl protecting groups.

As previously mentioned, the starting material in the present process is preferably an ester of the desired penicillin or cephalosporin. Whereas any convenient ester group can be used, it is desirable that the ester group chosen be one which is readily removed following the reaction process so as to provide easy access to the reaction products in the free acid form. Consequently, the particular ester chosen is conveniently one which has been previously employed as a carboxylic acid protecting group in the penicillin and cephalosporin art. Such ester moieties, which are readily cleavable include the p-nitrobenzyl, benzyl, benzhydryl, p-methoxybenzyl, 2,2,2-trichloroethyl, the esters formed with phenacyl halides such as phenacyl bromide, the tertiary butyl ester and like esters.

Such esters are removed according to published methods, for example, the 2,2,2-trichloroethyl ester is removed with zinc and acetic or formic acids as described in R. B. Woodward, et al., *J. Am. Chem. Soc.* 88, 852 (1966). The p-nitrobenzyl group is removed by hydrogenolysis under acidic conditions. The diphenylmethyl ester (benzhydryl) can be removed with trifluoroacetic acid in anisole at about 0 - 10° C. as described by British Pat. No. 1,041,985. The benzyl ester moiety can be removed by catalytic hydrogenolysis with hydrogen in the presence of palladium on carbon catalyst, for example, as described by U.S. Pat. No. 3,197,466. The t-butyl ester is removed according to the method described by *J. Org. Chem.*, 31, 444 (1966). The p-methoxybenzyl ester can be removed by following the procedure described by R. R. Chauvette, et al., *J. Org. Chem.*, 36, 1259 (1971).

The compounds of the invention, where $R_3$ of the substituted 3-carbon fragment $y$ in the Formula I is a 2-thiotetrazole, a 2-thio-1,3,4-thiadiazole or a 2-thio-1,3,4-oxadiazole substituent, are prepared in an alternative method by first reacting a 7-acylamidocephalosporanic acid ester (Formula II, $R_3$=acetoxy) in the process of the invention to obtain a 7-alkoxy substituted cephalosporanic acid ester intermediate. The 7-alkoxy substituted intermediate is thereafter reacted according to the conditions and procedures described in U.S. Patent 3,516,997 to effect the nucleophilic displacement of the 3-acetoxy substituent with the thiotetrazole, thio-1,3,4-thiadiazole or thio-1,3,4-oxadiazole. For example, p-nitrobenzyl 7-[2-(2-thienyl)acetamido]cephalosporanate is reacted in dry tetrahydrofuran at −80° C. with methyl lithium, excess methanol and t-butyl hypochlorite to provide p-nitrobenzyl 7-methoxy-7-[2-(2-thienyl)acetamido]cephalosporanate. The reaction product is isolated and is then reacted with hydrogen in an inert solvent in the presence of 5% Pd/c catalyst to effect hydrogenolysis of the p-nitrobenzyl ester and provide 7-methoxy-7-[2-(2-thienyl)acetamido]cephalosporanic acid. The latter product is then converted to its sodium salt in a dilute solution of sodium bicarbonate and the sodium salt reacted in a mixture of acetone and water containing sodium bicarbonate with 1-phenyl-IH-tetrazole-5-thiol to obtain 7-methoxy-3-(1-phenyl-IH-tetrazol-2-ylthiomethyl)-7-[2-(2-thienyl)acetamido]-3-cephem-4-carboxylic acid sodium salt.

The compounds of the invention, represented by the Formula I, wherein $R_3$ of the substituted 3-carbon fragment Y is pyridine, are prepared by heating a 7-alkoxy ($R_2O$-) cephalosporanic acid ($R_3$ is acetoxy) with pyridine in an inert solvent, for example acetone. Accordingly the 7-alkoxy, 7-cycloalkoxy, 7-allyloxy, 7-propargyloxy and 7-benzyloxycephalosporanic acids prepared in the present process can be converted to the corresponding pyridinium antibiotics. For example, 7-methoxy-7-[2(2-thienyl)acetamido]cephalosporanic acid is heated in acetone with pyridine to provide the 7-methoxy derivative of the well known antibiotic cephaloridine.

The starting materials (Formula II) in the process of this invention are known compounds or they can be prepared by methods known in the art. For example, the cephalosporanic acids, $R_3$=acetoxy, are prepared by the acylation of 7-aminocephalosporanic acid (7-ACA) with the desired acyl group,

Compounds wherein $R_3$ is a $C_3$-$C_4$ alkanoyloxy group can be prepared by the acylation of a 7-acylamidodesacetylcephalosporanic acid ester with a $C_3$- or $C_4$-alkanoic acid halide in the presence of a hydrogen halide acceptor. Likewise, the 3-carbamoyloxymethyl substituted compounds,

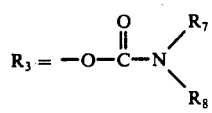

are prepared with the desacetylcephalosporins and the appropriate carbamoyl halide. The starting compounds, wherein $R_3$ is $C_1$-$C_4$ alkoxy, are prepared by reacting a 3-bromomethylcephalosporin with the appropriate $C_1$-$C_4$ alkyl metal alkoxide, for example, sodium methylate. Compounds wherein $R_3$ is $C_1$-$C_4$ thioalkyl, are prepared by reacting a cephalosporanic acid with a $C_1$-$C_4$ alkyl mercaptan in the presence of a weak base.

The acetoxymethyl esters of the compounds of Formula II, $R_9$= acetoxymethyl, can be prepared with the corresponding cephalosporin acid or penicillanic acid and a halomethyl acetate, such as chloromethyl acetate according to the method described in *The Journal of Antibiotics*, XXIV No. 11, 771 (1971).

Illustrative of the starting materials which can be employed in the present process are the acetoxymethyl and readily cleavable esters of the following acids: 6-Acetamidopenicillanic acid, 6-benzamidopenicillanic acid, 6-(2,6-dimethoxybenzamidopenicillanic acid, 6-phenylacetamidopenicillanic acid (Pen. G), 6-phenoxyacetamidopenicillanic acid (Pen V), 6-D-phenylglycylamidopenicillanic acid, 7-acetamidocephalosporanic acid, cephalosporin C, 7-acetamido-3-methyl-3-cephem-4-carboxylic acid, 7-phenoxyacetamidocephalosporanic acid, 7-mandelamidocephalosporanic acid, 7-D-phenylglycylamidocephalosporanic acid (cephaloglycin), 7-D-phenylglycylamido-3-methyl-3-cephem-4-carboxylic acid (cephalexin), 7-[2-(2-thienyl)acetamido]cephalosporanic acid (cephalothin), 7-mandelamido-3-(1-methyl-1H-tetrazole-5-ylthiomethyl)-3-cephem-4-carboxylic acid, 7-[2-(2-thienyl)acetamido]-3-(5-methyl-1,3,4-thiadiazol-2-ylthiomethyl)-3-cephem-4-carboxylic acid, 7-phenoxyacetamido-3-methoxymethyl-3-cephem-4-carboxylic acid, 7-phenoxyacetamido-3-methylthiomethyl-3-cephem-4-carboxylic acid, 7-[2-(2-thienyl)acetamido-3-N,N-dimethylcarbamoyloxymethyl-3-cephem-4-carboxylic acid, and 7-propionamido-3-(5-methyl-1,3,4-oxadiazol-2-ylthiomethyl)-3-cephem-4-carboxylic acid.

According to a further object of the present invention when a compound of the Formula II, wherein

represents the acyl moiety derived from mandelic acid or a substituted mandelic acid having an unprotected hydroxyl group, is employed in the process of this invention an intramolecular alkoxylation involving the unprotected hydroxyl group results to provide a spiro β-lactam compound of the Formula III.

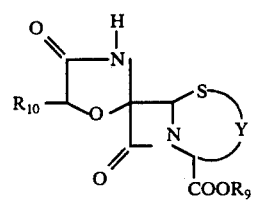

wherein $R_9$ and Y have the same meanings as defined in Formula II and $R_{10}$ represents phenyl, halophenyl, lower alkylphenyl, lower alkoxyphenyl an hydroxyphenyl as previously defined. For example, benzhydryl7-(2-hydroxy-2-phenylacetamido)-3-carbamoylmethyl-3-cephem-4-carboxylate is added to methyl lithium and excess methanol in dry tetrahydrofuran at a temperature of −78° C. and 1.2 equivalents of t-butyl hypochlorite are added to the cold reaction mixture.

The mixture is stirred in the cold for 3 minutes and is then acidified with 98% formic acid to provide the compound of Formula III wherein $R_{10}$ is phenyl and $R_9$ is benzhydryl. Hydrogenolysis of the benzhydryl ester affords the free acid, 3-carbamoyloxymethyl-4'-oxo-5'-phenyl spiro[3-cephem-7,2'-oxazolidine]4-carboxylic acid of the formula

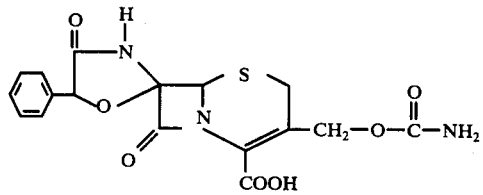

The spiro β-lactam esters of the Formula III are converted to the corresponding acids by removal of the ester forming group $R_9$ according to conventional procedures such as hydrogenolysis and acid hydrolysis.

The spiro β-lactam acids are useful antibiotic compounds possessing significant activity against the gram positive organisms. When administered parenterally the spiro β-lactam acids of the alkali metal salts thereof, for example the sodium salt, are useful in combatting gram positive infections in warm blooded mammals.

Illustrated of the spiro β-lactam compounds provided by this invention are the following:

3-acetoxymethyl-4'-oxo-5'-phenylspiro[3-cephem-7,2'-oxazolidine]-4-carboxylic acid, 3-methyl-4'-oxo-phenylspiro-[3-cephem-7,2'-oxazolidine]-4-carboxylic acid, 3-acetoxymethyl-4'-oxo-5'-(4-chlorophenyl)spiro-[3-cephem-7,2'-oxazolidine]4-carboxylic acid, benzhydryl 3-methyl-4'-oxo-5'-(4-hydroxyphenyl)-spiro[3-cephem-7,2'-oxazolidine]4-carboxylate, benzhydryl 2,2-dimethyl-4'-oxo-5'-phenylspiro[penam-6,2'oxazolidine]-3-carboxylate, 2,2-dimethyl-4'-oxo-5'-(4-methoxyphenyl)-spiro-[penam-6,2'-oxazolidine]-3-carboxylic acid, and like spirooxazolidinone penicillins and cephalosporins.

The preparation, in situ, of an anionic form of the 6-acylamidopenicillanic acid esters and the 7-acylamido-3-substituted methyl-3-cephem-4-carboxylic acid esters, the cephalosporin esters, is a significant aspect of the present invention. The preparation of such anionic forms of these antibiotics followed by the reaction of the anion with a positive halogen makes possible the subsequent nucleophilic substitution on the β-lactam carbon atom.

It will be appreciated by those skilled in the art that other anion gathering bases can be employed in the initial phase of the above described process for the preparation of the anionic forms of the penicillins and cephalosporins. One such anion generator which can be employed is lithium diisopropyl amide.

The compounds provided by the process of this invention are useful antibiotic substances which inhibit the growth of microorganisms pathogenic to animal and plant life. For example, in standard in vitro tests, the compounds of the invention demonstrate significant activity against the following illustrative microorganisms: *Staphylococcus aureus, Bacillus subtilis, Sarcina lutea, Escherichia coli, Klebsiella pneumoniae, Proteus vulgaris, Salmonella gallinarium, Serratia marcescens* and *Pseudomonas solanacearum*.

In general, the 6-substituted penicillins and the 7-substituted cephalosporins provided by this invention demonstrate increased activity against the gram-negative microorganisms in comparison to the unsubstituted antibiotics. The activity vs the gram-positive organisms on the other hand is somewhat less than that exhibited by the unsubstituted penicillins and cephalosporins. However, the especially preferred compounds provided herein, demonstrate increased activity against the gram-negative microorganisms while yet retaining the activity against the gram-positive organisms which is demonstrated by the unsubstituted cephalosporin antibiotics. The antibacterial activity of the especially preferred compounds is illustrated by the data presented in Table I and II for two such preferred compounds.

The following Table I lists the minimum inhibitory concentrations (MIC) for two of the compounds of the invention against five clinical isolates of penicillin resistant *Staphylococcus aureus* both in the presence and absence of serum. The MIC values were determined by the Gradient Plate method carried out essentially as described by Bryson and Szybalski, Science, 116, 45-46 (1952).

Table I

| | Antibiotic Activity vs. Penicillin Resistant *Staphylococcus aureus* | | | | | | | | | |
|---|---|---|---|---|---|---|---|---|---|---|
| | Staphylococcus Clinical Isolates MIC(mcg/ml) | | | | | | | | | |
| | V41 | | V32 | | X400 | | V84 | | X1.1 | |
| Compound[1] | NS[2] | S[3] | NS | S | NS | S | NS | S | NS | S |
| A | 4.2 | 6.7 | 4.5 | 7.6 | 16.6 | 15.4 | 3.1 | 2.0 | 0.5 | <0.1 |
| B | 1.5 | 1.1 | 1.8 | 2.0 | 10.0 | 9.5 | 0.6 | 1.0 | 0.4 | 0.5 |

[1]A = 7-Mandelamido-7-methoxy-3-(1-methyl-1H-tetrazol-5-ylthiomethyl)-3-cephem-4-carboxylic acid.
B = 7-[2-(2-Thienyl)acetamido]-7-methoxy-3-(1-methyl-1H-tetrazol-5-ylthiomethyl)-3-cephem-4-carboxylic acid.
[2]NS = absence of serum.
[3]S = presence of serum.

In Table II which follows, the antibiotic activity against exemplary gram negative organisms is illustrated by the activity demonstrated by two of the preferred compounds. The activity, expressed in terms of the minimum inhibitory concentration, was determined by the Gradient Plate technique.

Table II

| Antibiotic Activity vs. Gram-Negative Microorganisms | | |
|---|---|---|
| | Compound[1] MIC(mcg/ml) | |
| Organism | A | B |
| *Shigella* sp. | 2.0 | 6.6 |
| *Escherichia coli* | 2.5 | 7.9 |
| *Klebsiella pneumoniae* | 0.6 | 0.5 |
| *Aerobacter aerogenes* | 0.7 | 3.5 |
| *Salmonella heidelberg* | 0.6 | 0.9 |
| *Pseudomonas aeruginosa* | >200 | >200 |
| *Serratia marcescens* | 3.4 | 5.4 |

[1]A = 7-Mandelamido-7-methoxy-3-(1-methyl-1H-tetrazol-5-ylthiomethyl)-3-cephem-4-carboxylic acid.
B = 7-[2-(2-Thienyl)acetamido]-3-(1-methyl-1H-tetrazol-5-ylthiomethyl)-3-cephem-4-carboxylic acid.

In the following Table III the antibiotic activity of the compounds of the invention is further illustrated by the activity shown for representative compounds as determined by the standard disc-plate method.

Table III

| In vitro Antibiotic Spectrum Disc-Plate Method | | | |
|---|---|---|---|
| | Diameter of Zone of Inhibition(mm) concentration(mg/ml) | | |
| | Test Compound[1] | | |
| Test Organism | C | D | E |
| Staphylococcus aureus | 24/0.5 | 24/0.5 | 25/0.1 |
| Bacillus subtilis | 25/0.5 | 24/0.5 | 22/0.1 |
| Sarcina lutea | 23/0.5 | 23/0.5 | 24/0.1 |
| Mycobacterium avium | 10/0.5 | 20/5.0 | 15/1.0 |
| Proteus vulgaris | 21/0.5 | 18/0.5 | 18/0.1 |
| Salmonella gallinarum | 26/0.5 | 25/0.5 | 20/1.0 |
| Escherichia coli | 23/0.5 | 20/0.5 | 22/0.1 |
| Klebsiella pneumoniae | 19/0.5 | 17/0.5 | 16/0.1 |
| Serratia marcescens | 19/0.5 | 17/0.5 | 18/1.0 |
| Pseudomonas solanacearum | 16/0.5 | 23/0.5 | 16/1.0 |

[1] C = 7-[2-(1-tetrazolyl)acetamido]-7-methoxy-3-(5-methyl-1,3,4-thiadiazol-2-ylthiomethyl)-3-cephem-4-carboxylic acid
D = 7-[2-(1-Tetrazolyl)acetamido]-7-methoxy-3-acetoxymethyl-3-cephem-4-carboxylic acid.
E = 7-Mandelamido-7-methoxy-3-(5-methyl-1,3,4-thiadiazol-2-ylthiomethyl)-3-cephem-4-carboxylic acid.

The substituted penicillins and cephalosporins provided by this invention are useful antibiotic compounds which are effective in combatting infections in warm blooded mammals. When administered parenterally at a non-toxic dose between about 2.5 and 750 mg./kg. of body weight, the compounds of the invention are effective in combatting bacterial infections in warm-blooded mammals. As is recognized with other antibiotics, the dose required in the treatment of a particular host varies. For example, depending on such circumstances as the severity of the infection, the general health and physical condition of the particular host and the variability in response of the particular host, the amount of antibiotic administered will vary. Likewise, a treatment regime comprising multiple doses, for example, 3 or 4 doses administered daily, may be desirable with a particular host. Alternatively, a compound of the invention can be administered as a single daily dose, which regime may continue until the desired response has been attained.

The compounds of the invention, represented by the Formula I, which are esters other than the acetoxymethyl esters, or which contain a protected hydroxy or a protected amino function do not possess antibiotic activity to any appreciable degree. However, by removal of the ester group or by removal of the hydroxy and amino function protecting groups, by employing well known methods and procedures, the antibiotic compounds of the invention are obtained where in the Formula I $R_1$ is hydrogen and a free amino or free hydroxy group is present.

The following examples more fully illustrate the present invention without any intention to be limiting thereof.

In the following examples, infared absorption spectrum and nuclear magnetic resonance spectrum are abbreviated IR and NMR respectively. Only the significant IR absorption attributable on the carbonyl function of the β-lactam ring is given. Likewise, the pertinent peaks observed in the NMR spectra are listed. The nuclear magnetic resonance spectra were obtained on a Varian Associates T-60 Spectrometer with tetramethylsilane as the reference standard. The values listed are in cycles per second (c.p.s.).

The following standard abbreviations are employed for the observed peaks in the NMR spectra: $s$ = singlet; $m$ = multiplet; $q$ = quartet; $d$ = doublet.

EXAMPLE 1

To 25 ml. of dry tetrahydrofuran maintained at ice bath temperature were added 2.2 ml. of methyl lithium (1.58 M.) and 4 ml. of dry methanol. The solution was stirred under nitrogen for about 2 minutes and was then cooled to a temperature of about −80° C. by means of a dry ice-acetone bath. To the cold solution was added a solution of 531 mg. of p-nitrobenzyl 7-[2-(2-thienyl) acetamido]cephalosporanate in 8 ml. of dry tetrahydrofuran and the reaction mixture stirred in the cold for 2 minutes. To the cold reaction mixture was then added 0.143 ml. (1.2 equivalents) of t-butyl hypochlorite, and the reaction mixture was stirred for 10 minutes after the addition of the chlorinating agent was complete. The reaction mixture was then quenched by adding 4 ml. of glacial acetic acid. The reaction mixture was then evaporated in vacuo and the residue dissolved in dichloromethane. The solution of the residue was washed three times with a saturated solution of sodium chloride, one time with a dilute solution of sodium thiosulfate, two times with a solution of sodium bicarbonate and thereafter one time with a saturated solution of sodium chloride. The washed solution was then dried and evaporated in vacuo to provide 536 mg. of substantially pure p-nitrobenzyl 7-methoxy-7-[2-(2-thienyl)acetamido]-cephalosporanate.

I.R. (KBr) $1780^{cm-1}$
N.M.R. (CDCl$_3$):
  200–210 (m, 2H, C$_2$),
  298 (q, 2H, —CH$_2$OAc),
  3 302 (s, 1H, C$_6$)
  231 (s, 2H, amide methylene)
  4.3-436 (m, 3H, thienyl protons)
  420 (s, 2H, ester methylene)
  470 (q, 4H, aromatic)
  123 (s, 3H, acetoxy methyl)
  207 (m, 3H, 7-methoxy).

The p-nitrobenzyl ester was cleaved to provide the free acid in the following manner. A suspension of 260 mg. of 5 percent Pd/C in 15 ml. of 1:1 methanol:tetrahydrofuran was prehydrogenated for one hour. To the suspension was added a solution of 260 mg. of the p-nitrobenzyl ester in 15 ml. of 1:1 methanol:tetrahydrofuran and the mixture was hydrogenated for 3 hours in an atmosphere of hydrogen gas. The catalyst was filtered and the filtrate was evaporated to provide a solid residue. The residue was dissolved in ethyl acetate and the acidic reduction product was extracted with a dilute solution of sodium bicarbonate. The bicarbonate extracts were made acid to pH 2.5 by the addition of dilute hydrochloric acid and were then extracted with ethyl acetate. The extact was dried and thereafter evaporated in vacuo to yield 182 mg. of 7-methoxy-7-[2-(2-thienyl)acetamido]cephalosporanic acid.

I.R. (KBr): $1778^{cm-1}$
NMR (100 mcg.):
  285–296 (m, 2H, C$_2$),
  496–515 (m, 2H, —CH$_2$—OAc),
  496–515 (m, IH, C$_6$),
  693–705 (m, IH, amide NH),
  391 (S, 2H, amide methylene),
  696–728 (m, 3H, thienyl protons),
  158 (s, 3H, acetoxy methyl)
  348 (m, 3H, 7-methoxy).

EXAMPLE 2

To 25 ml. of cold, dry, tetrahydrofuran maintained under an atmosphere of nitrogen were added 2.2 ml. of 1.58 M. methyl lithium and 4 ml. of dry methanol. The solution was stirred for several minutes and was then cooled to about −80° C. by means of a dry ice-acetone bath. To the cold solution was added 480 mg. of benzhydryl 7-acetamidocephalosporanate in 8 ml. of dry tetrahydrofuran. The reaction mixture was stirred for approximately 2 minutes and then 0.143 ml. (1.2 equivalents) of t-butyl hypochlorite was added with stirring. After the reaction mixture was stirred for approximately 10 minutes, the reaction was quenched by the addition of 4 ml. of glacial acetic acid. The reaction mixture was evaporated to dryness and the residue was dissolved in dichloromethane. The solution was washed successively with a saturated solution of sodium chloride, a dilute solution of sodium thiosulfate, a saturated solution of sodium bicarbonate, and a saturated solution of sodium chloride. The washed solution was then dried and evaporated to dryness to yield 541 mg. of crude benzhydryl 7-acetamido-7-methoxycephalosporanate.

I.R. (CHCl$_3$): 1790$^{cm-1}$
N.M.R. (acetone d$_6$):
  304 (s, IH, C$_6$)
  209 (s, 3H, 7-methoxy)

The benzhydryl ester was cleaved by reacting the ester with a 50:50 mixture of trifluoroacetic acid and 98% formic acid to provide a solid residue containing 7-acetamido-7-methoxycephalosporanic acid.

N.M.R. (Acetone d$_6$):
  306 (s, IH, C$_6$)
  209 (s, 3H, 7-methoxyl).

EXAMPLE 3

In accordance with the procedures described by Example 1, benzhydryl 3-methoxymethyl-7-[2-(2-thienyl)-acetamido]-3-cephem-4-carboxylate was reacted at a temperature of −80° C. with methyl lithium in the presence of methanol and t-butyl hypochlorite to provide benzhydryl 3-methoxymethyl-7-methoxy-7-[2-(2-thienyl)acetamido]-3-cephem-4-carboxylate.

I.R. (KBr): 1780$^{cm-1}$
N.M.R. (CDCl$_3$):
  303 (s, IH, C$_6$)
  200-210 (m, 3H, 7-methoxyl).

The above ester was hydrolyzed under acidic conditions in the following manner. To 150 mg. of the ester in a 50 ml. round bottom flask maintained at a temperature of approximately −10° C. was added 2.5 ml. of a 1:1 mixture of trifluoroacetic acid:formic acid. To the stirred mixture was added 30 ml. of dichloromethane. The reaction mixture was then evaporated to remove solvents and the residue was dissolved in ethyl acetate. The antibiotic acid was extracted from the ethyl acetate solution with a saturated solution of sodium bicarbonate. The bicarbonate extract was acidified to pH 2.5 by the addition of hydrochloric acid and the acidified solution was thereafter extracted with ethyl acetate. The ethyl acetate extract was dried and then evaporated in vacuo to provide 60 mg. of 3-methoxymethyl-7-methoxy-7-[2-(2-thienyl)-acetamido]-3-cephem-4-carboxylic acid.

N.M.R. (CDCl$_3$):
  304 (s, IH, C$_6$)
  200-210 (m, 3H, 7-methoxyl).

EXAMPLE 4

To 25 ml. of dry tetrahydrofuran maintained at about 0° C. was added 3 ml. of 1.58 M. methyl lithium and 6 ml. of dry methanol. The solution was stirred for about 5 minutes and was then cooled to approximately −80° C. by means of a dry ice-acetone bath. To the cold solution was added a solution of 582 mg. of p-nitrobenzyl 3-methyl-7-(2-t-butyloxycarboxamido-2-phenylacetamido)-3-cephem-4-carboxylate in 8 ml. of dry tetrahydrofuran and the reaction mixture stirred for 2 minutes following the addition. To the reaction mixture was then added 0.143 ml. of t-butyl hypochlorite and the reaction mixture was stirred for 10 minutes following the addition of the hypochlorite. The reaction was then quenched by the addition of 6 ml. of 98% formic acid. The quenched reaction mixture was evaporated in vacuo and the residue dissolved in dichloromethane. The solution was washed consecutively with a saturated solution of sodium chloride, dilute aqueous sodium thiosulfate, a saturated solution of sodium bicarbonate and finally with a saturated sodium chloride solution. The washed solution was then evaporated in vacuo to dryness to provide p-nitrobenzyl 7-methoxy-3-methyl-7-(t-butyloxycarboxamido-2-phenylacetamido)-3-cephem-4-carboxylate.

I.R. (KBr): 1785 cm$^{-1}$
N.M.R. (CDCl$_3$):
  212 (s, 3H, 7-methoxyl)
  304 (s, IH, C$_6$)

To a solution of 350 mg. of the amino protected ester prepared as described above in a 1:1 mixture of methanol: tetrahydrofuran was added 350 mg. of 5% palladium or carbon catalyst which had been prereduced. The suspension was stirred in an atmosphere of hydrogen for 3 hours at room temperature. The catalyst was filtered, and the filtrate evaporated to dryness. The residue obtained was dissolved in ethyl acetate and the solution was washed with an aqueous solution of sodium bicarbonate. The bicarbonate wash was acidified to pH 2.5 with hydrochloric acid and the acidified solution was extracted with ethyl acetate. The ethyl acetate extract was dried over sodium sulfate and thereafter evaporated to dryness to yield 210 mg. of 3-methyl-7-methoxy-7-(2-t-butyloxycarbamido-2-phenylacetamido)-3-cephem-4carboxylic acid. The acid thus obtained was dissolved in 2 ml. of cold trifluoroacetic acid and the solution stirred for 5 minutes. The cold acid solution was then added by dropwise addition to diethyl ether to precipitate the trifluoroacetic acid salt of 3-methyl-7-methoxy-7-(2-amino-2-phenylacetamido)-3-cephem-4-carboxylic acid.

N.M.R. (100 mcg., D$_2$O):
  394 (s, 3H, 7-methoxyl)
  561 (s, IH, C$_6$).

EXAMPLE 5

According to the procedure described by Example 4, 479 mg. of 2,2,2-trichloroethyl 3-methyl-7-phenoxyacetamido-3-cephem-4-carboxylate was reacted with methanol, methyl lithium and t-butyl hypochlorite in anhydrous tetrahydrofuran at −80° C. to provide 2,2,2-trichloroethyl 3-methyl-7-methoxy-7-phenoxyacetamido-3-cephem-4-carboxylate.

I.R. (CHCl$_3$): 1780 cm$^{-1}$
N.M.R. (CDCl$_3$): 214 (s, 3H, 7-methoxyl)

The trichloroethyl ester prepared as described above was hydrolyzed in the following manner. To a cold, 0°

C. solution of 200 mg. of the ester in 1 ml. of dimethylformamide was added 0.3 ml. of 98% formic acid and 220 mg. (9 equivalents) of zinc dust, and the mixture stirred for 1.5 hours. The zinc was filtered and washed with water and ethyl acetate. The water layer of the filtrate was acidified to pH 2.5 by the addition of 5% hydrochloric acid. The ethyl acetate layer and the acidified aqueous layer were shaken vigorously and separated. The ethyl acetate layer was then washed with aqueous sodium bicarbonate and the bicarbonate wash was then acidified to pH 2.5 by the addition of hydrochloric acid. The acidified was was extracted with ethyl acetate and the extract dried and then evapoated in vacuo to give 70 mg. of 3-methyl-7-methoxy-7-phenoxyacetamido-3-cephem-4-carboxylic acid.

N.M.R. (CDCl$_3$):
  213 (s, 3H, 7-methoxyl)
  305 (s, IH, C$_6$).

EXAMPLE 6

To 200 ml. of dry tetrahydrofuran maintained at 0 to 5° C. was added with stirring 20 ml. of 1.58 M. methyl lithium. To this solution was added cautiously 40 ml. of dry methanol with stirring. The solution was then cooled with stirring to −80° C. by means of a dry ice-acetone bath. To the cold solution was added by dropwise addition under nitrogen a solution of 4.69 g. of p-nitrobenzyl 6-phenylacetamidopenicillanate in 80 ml. of dry tetrahydrofuran. The reaction mixture was stirred for 3 minutes in the cold and then 1.43 ml. (1.2 equivalents) of t-butyl hypochlorite was added with stirring. The reaction was allowed to stir for about 25 minutes and was then quenched by the addition of 40 ml. of 98% formic acid.

The reaction mixture was then evaporated in vacuo to a volume of 50 ml. The liquid concentrate was poured into a saturated solution of sodium chloride which was layered with dichloromethane. The organic layer was separated and the aqueous salt layer was washed with dichloromethane. Both dichloromethane layer were combined and washed with a saturated solution of sodium chloride, a saturated solution of sodium bicarbonate, and finally again with a saturated sodium chloride solution. The washed organic layer containing the reaction product mixture was then dried over sodium sulfate and evaporated to provide 5.1 g. of crude reaction product mixture.

The crude reaction product mixture, 5.1 g., was dissolved in 100 ml. of benzene and the solution was chromatographed over a column packed with 300 g. of silica/15% water. The column was eluted initially with 10% benzene in ethyl acetate. The concentration of benzene was gradually increased to 20% benzene. Sixty fractions of 175 ml. volume were collected. Fractions 34 to 45 and 47 to 50 were combined and evaporated to dryness to provide 2.83 g. of p-nitrobenzyl 6-methoxy-6-phenylacetamidophenicillanate.

I.R. (CHCl$_3$): 1778 cm $^{-1}$
N.M.R. (CDCL$_3$):
  84 (s, 6H, 2,2-dimethyl)
  267 (s, IH, C$_3$)
  333 (s, IH, C$_5$)
  396 (s, IH, amide proton)
  219 (s, 2H, amide methylene)
  438 (s, 5H, phenyl protons)
  316 (s, 2H, ester methylene)
  468 (q, 4H, nitrophenyl protons)
  204 (s, 3H, 6-methoxyl)

A solution of 200 mg. of the above ester in 15 ml. of 1:1 tetrahydrofuran:methanol was added to a suspension of 200 mg. of 5% palladium on carbon in a 1:1 mixture of tetrahydrofuran:methanol which had been prehydrogenated for 1 hour. The solution was agitated in an atmosphere of hydrogen at room temperature for 3 hours. The catalyst was filtered and the filtrate evaporated in vacuo to obtain a solid residue. The residue was dissolved in ethyl acetate and the solution was extracted with a saturated solution of sodium bicarbonate. The bicarbonate extract was separated and acidified to pH 2.0 with dilute hydrochloric acid. The acidified solution was then extracted with ethyl acetate and the extract dried over sodium sulfate. The dried extract was then evaporated to dryness to yield 130 mg. of 6-methoxy-6-phenylacetamidopenicillanic acid.

N.R.R. (CDCL$_3$):
  85 (d, 6H, 2,2-dimethyl)
  261 (s, IR, C$_3$)
  332 (s, IH, C$_5$)
  615 (s, IH, amide proton)

EXAMPLE 7

According to the alkoxylation procedure described by the foregoing examples, 584 mg. of p-nitrobenzyl 6-(2-t-butyloxycarbamido-2-phenylacetamido)penicillanate was reacted with methyl lithium, methanol, and t-butyl hypochlorite in anhydrous tetrahydrofuran at −80° C. to provide following the workup employed in the foregoing examples, 512 mg. of p-nitrobenzyl 6-methoxy-6-(2-t-butyloxycarbamido-2-phenylacetamido)penicillanate.

N.M.R. (CDCl$_3$):
  211 (s, 3H, 6-methoxy)
  337 (s, IH, C$_5$).

To a solution of 205 mg. of the methoxylated ester obtained as described above in 15 ml. of a 1:1 mixture of tetrahydrofuran and methanol was added a suspension of 205 mg. of 5% palladium on carbon catalyst in a 1:1 mixture of tetrahydrofuran and methanol which ws previously hydrogenated. The suspension was reacted with hydrogen at room temperature for 3hours. The catalyst was filtered and the filtrate was evaporated in vacuo. The solid residue obtained was dissolved in ethyl acetate and the acidic reaction product extracted therefrom with a saturated solution of sodium bicarbonate. The bicarbonate extract was acidified to pH 2.5 with hydrochloric acid, and the acidic reaction product back extracted into ethyl acetate. The ethyl acetate extract was dried and then evaporated in vacuo to yield 130 mg. of 6-methoxy 6-(2-t-butyloxycarbamido-2-phenylacetamido)penicillanic acid.

To a solution of 110 mg. of the above prepared amino protected penicillanic acid in 25 ml. of acetonitrile was added a solution of 50 mg. of p-toluene sulfonic acid in 5 ml. of acetonitrile. The reaction mixture was stirred at room temperature for 3 hours and was thereafter diluted with 3 ml. of water. The pH of the solution was adjusted to pH 4.7 with triethylamine and the volume of the reaction mixture was reduced by one half. On standing in the refrigerator a crystalline precipitate of 6-methoxy-6-(2-amino-2-phenylacetamido)penicillanic acid was obtained.

EXAMPLE 8

According to the procedures described by the foregoing examples, 515 mg. of p-nitrobenzyl 6-(2,6-dimethoxybenzamido) penicillanate was reacted with methyl lithium, methanol, and t-butyl hypochlorite in anhydrous tetrahydrofuran at −80° C. to provide 6-methoxy-6-(2,6-dimethoxybenzamido)penicillanic acid p-nitrobenzyl ester.

I.R. (CHCl$_3$): 1778$^{cm-1}$
N.M.R. (CDCl$_3$):
216 (s, 3H, 6-methoxyl)
336 (s, 1H, C$_5$).

Hydrogenolysis of the ester thus prepared, according to the procedure previously described, provided 93 mg. of 6-methoxy-(2,6-dimethoxybenzamido)penicillanic acid.
N.M.R. (CDCl$_3$):
214 (s, 3H, 6-methoxyl)
332 (s, 1H, C$_5$)

EXAMPLE 9

To 70 ml. of dry benzene containing 0.1 g. of p-toluene sulfonic acid was added 1.14 g. of benzhydryl 7-(2-hydroxy-2-phenylacetamido)cephalosporanate with stirring. To the stirred solution 0.144 g. of ethyl vinyl ether was slowly added by dropwise addition. The reaction mixture was evaporated in vacuo and the residue dissolved in ethyl acetate. The solution was washed with cold water, dried and evaporated to provide in a nearly quantitative yield the hydroxy protected cephalosporanic ester, benzhydryl 7-[2-(1-ethoxyethoxy)-2-phenylacetamido]cephalosporanate.

The protected hydroxy cephalosporanic ester thus prepared was reacted according to the procedures described in the foregoing examples with lithium methoxide, methanol, and t-butyl hypochlorite in anhydrous tetrahydrofuran at −80° C. to provide benzhydryl 7-methoxy-7-[2-(1-ethoxyethoxy)-2-phenylacetamido]-cephalosporanate. The product was purified by chromatography over silica gel during which partial deblocking of the protected hydroxyl group occurred to provide a mixture containing 35% of the purified reaction product and 20% of the de-blocked reaction product 7-methoxy-7-(2-hydroxy-2-phenylacetamido)cephalosporanate. The purified mixture was reacted with a mixture of trifluoroacetic acid and 98% formic acid to effect removal of both the hydroxyl protecting group and the benzhydryl ester group to provide 7-methoxy-7-(2-hydroxy-2-phenylacetamido)cephalosporanic acid.
N.M.R. (CDCl$_3$)
122 (s, 3H, acetoxy methyl)
204 (s, 3H, 7-methoxyl).

EXAMPLE 10

According to the reaction procedures described by the foregoing Examples the following compounds are prepared with the indicated reactants. In each instance tetrahydrofuran is the preferred solvent and t-butyl hypochlorite is the preferred chlorinating agent. Listed in the order of appearance are the reaction product, the alkali metal alkoxide, the corresponding alcohol and the starting penicillin ester of cephalosporin ester.

3-methylthiomethyl-7-ethoxy-7-(2-amino-2-phenylacemido)-3-cephem-4-carboxylic acid; lithium ethoxide; absolute ethanol;p-nitrobenzyl 3-methylthiomethyl-7-(2-amino-2-phenylacetamido)-3-cephem-4-carboxylate.

3-carbamoyloxymethyl-7-isopropoxy-7-(2-phenoxyacetammido)-3-cephem-4-carboxylic acid; lithium isopropoxide; isopropyl alcohol; 2,2,2-trichloroethyl 3-carbamoyloxmethyl-7-(2-phenoxy acetamido)-3-cephem-4-carboxylate.

7-Allyloxy-3-methyl-7-[2-(2-thienyl)acetamido]-3-cephem--4-carboxylic acid; potassium allyloxide; allyl alcohol; benzhydryl 3-methyl-7-[2-(2-thienyl)acetamido]-3-cephem-4-carboxylate.

7-cyclopropoxy-3-ethoxymethyl-7-(2-phenoxyacetamido)-3-cephem-4-carboxylate; lithium cyclopropoxie; cyclopropyl alcohol; p-nitrobenzyl 3-ethoxymethyl-7-(2-phenoxyacetamido)-3-cephem-4-carboxylate.

7-benzyloxy-3N-methylcarbamoyloxymethyl-7-(2-phenyl-mercaptoacetamido)-3-cephem-4-carboxylic acid; lithium benzyloxide; benzyl alcohol; 2,2,2-trichloroethyl 3-N-methylcarbamoyloxymethyl-7-(2-phenylacetamido)-3-cephem-4-carboxylate.

EXAMPLE 11

To 25 ml. of anhydrous tetrahydrofuran maintained in an atmosphere of nitrogen and at a temperature of 0° C. were added with stirring 2.2 ml. of 1.65 N methyl lithium and 4 ml. of dry methanol. The solution was stirred for 5 minutes and was then cooled to a temperature of −80° C. To the cold solution was added 573 mg. of benzhydryl 7-(2-hydroxy-2-phenylacetamido)-3-carbamoyloxymethyl-3-cephem-4-carboxylate and stirring was continued for several minutes before 0.143 ml. of t-butyl hypochlorite was added. The reaction mixture was stirred for an additional 20 minutes at −80° C. before the reaction was quenched by the addition of 4 ml. of glacial acetic acid. The reaction mixture was then evaporated to remove solvents and the residue dissolved in dichloromethane. The solution of the residue was washed consecutively with a saturated solution of sodium chloride, a dilute solution of sodium thiosulfate, a saturated solution of sodium bicarbonate and finally again with a saturated solution of sodium chloride. The washed solution was dried and evaporated to provide 604 mg. of the crude reaction product mixture containing benzhydryl 3-carbamoyloxymethyl-4'-oxo-5'-phenylspiro-[3-cephem-7,2'-oxazolidine]-4-carboxylate. The crude mixture was purified on silica coated preparative thin layer plates using a 50:50 ethyl acetate:benzene solvent system for development. The spot on the chromatogram containing the reactive product was scraped from the plate and the product was separated from the silica by extraction with ethyl acetate to provide 375 mg. of the purified benyhydryl ester.

EXAMPLE 12

To 1 ml. of a cold 50:50 mixture of trifluoroacetic acid and 98% formic acid was added 100 mg. of the purified benzhydryl ester prepared as described by Example 11. After one minute, 10 ml. of dichloromethane were added and the solution was evaporated under vacuum to a small volume. The concentrate was dissolved in ethyl acetate and the acidic reaction product was extracted with an aqueous solution of sodium bicarbonate. The bicarbonate extract was acidified to pH 2.5 and the reaction product was back extracted with ethyl acetate. The extract was dried and evaporated to obtain 66 mg. of 3-carbamoyloxymethyl-4'-oxo-5'-phenylspiro-[3-cephem-7,2'-oxazolidine]-4-carboxylic acid as a solid in substantially pure form.

EXAMPLE 13

To a solution of 1.5 g. of sodium 7-methoxy-7-(2-phenoxyacetamido)-3-acetoxymethyl-3-cephem-4-carboxylate in 50 ml. of water was added 1 equivalent of sodium hydroxide and 1 equivalent of 2-thiol-1,3,4- thiadiazole. The mixture was heated at a temperature of 70° C. for five hours and was then acidified with 1N hydrochloric acid. The reaction product was extracted from the acidified mixture with ethyl acetate and the extract was washed with water and evaporated to dryness. The solid residual product was crystallized from a mixture of ethyl acetate and DMF to yield 7-methoxy-7-(2-phenoxyacetamido)-3-(1,3,4-thiadiazol-2-ylthiomethyl)-3-cephem-4-carboxylic acid in substantially pure form.

EXAMPLE 14

According to the procedure described by Example 13, sodium 7-ethoxy-7-[2-(2-thienyl)acetamido]-3-acetoxymetyl-3-cephem-4-carboxylate was reacted in water with 2-thiol-1-methyl-1H-tetrazole to yield 7-[2-(2-thienyl)acetamido]-3-(1-methyl-1H-tetrazol-5-ylthiomethyl)-3-cephem-4-carboxylic acid.

EXAMPLE 15

7-Methoxy-7-mandelamido-3-(5-methyl-1,3,4-thiadiazol-2-ylthiomethyl-3-cephem-4-carboxylic acid To a solution of 912 mg of sodium 7-methoxy-7-mandelamido-3-acetoxymethyl-3-cephem-4-carboxylate, prepared by the method described by Example 9, in 1 ml of water was added a solution of sodium hydroxide to adjust the pH of the solution to pH 6.5. To the solution was added 10 mg of 2-mercapto-5-methyl-1,3,4-thiadiazole and the reaction mixture was heated with stirring for 3 hours at 70° C. The reaction mixture was cooled and was then acidified with dilute hydrochloric acid. The acidified mixture was extracted with ethyl acetate containing 10% by volume of tetrahydrofuran and was then dried over magnesium sulfate and evaporated to dryness to yield the reaction product mixture containing 7-methoxy-7-mandelamido-3-(5-methyl-1,3,4-thiadiazol-2-ylthiomethyl)-3-cephem-4-carboxylic acid.

The dry residue was dissolved in tetrahydrofuran and 400 mg of diphenyldiazomethane were added to the solution. The solution was stirred at room temperature for 12 hours and was then evaporated to a solid residue. The residue was leeched with a mixture of chloroform:petroleum ether which on evaporation to dryness afforded one gram of a solid foam residue.

The residue was chromatographed on preparative thin layer silica gel plates with ethyl acetate:benzene (50:50), to yield 229 mg of the diphenylmethyl ester of the starting material, and 188 mg of diphenylmethyl 7-methoxy-7-mandelamido-3-(5-methyl-1,3,4-thiadiazol-2-ylthiomethyl)-3-cephem-4-carboxylate.

The diphenylmethyl ester of the reaction product, 188 mg, was dissolved in 2 ml of 97 percent formic acid and the solution was stirred at room temperature for 75 minutes. The reaction mixture was treated with benzene and evaporated. More benzene was added to the residue and the mixture was again evaporated to dryness. The dry residue was partially dissolved in ethyl acetate and a saturated solution of sodium bicarbonate was added. The bicarbonate layer was separated, washed with ethyl acetate and acidified to pH 2.0 with hydrochloric acid. The acidified solution was then extracted with ethyl acetate containing 10% by volume of tetrahydrofuran. The extract was dried and was evaporated to dryness to yield 76 mg of 7-methoxy-7-mandelamido-3-(5-methyl-1,3,4-thiadiazol-2-ylthiomethyl)-3-cephem-4-carboxylic acid having the following NMR spectrum (acetone $d_6$):

215 (q, 2H, $C_2$)
267 (q, 2H, $C_3$)
306 (s, 1H, $C_6$)
205 (s, 3H, $C_7$ methoxy)
492 (s, 1H, amide N-H)
315 (s, 1H, amide C-H)
375 (s, 2H, $C_3$ $CH_2$-S)
430-460 (m, 5H, aromatic)
162 (s, 3H, thiadiazole-5-methyl group).

EXAMPLE 16

7-Methoxy-7-[2-(2-thienyl)acetamido]-3-(1-methyltetrazol-5-ylthiomethyl)-3-cephem-4-carboxylic acid To a solution of 900 mg of sodium 7-methoxy-7-[2-(2-thienyl)acetamido]-3-acetoxymethyl-3-cephem-4-carboxylate, prepared by the method described in Example 1, in 10 ml of water was added a solution of sodium hydroxide to adjust the pH of the solution to pH 6.5. To the solution was added 232 mg of 1-methyltetrazole-5-thiol and the mixture was heated with stirring for 3 hours at 70° C.

The pH of the reaction mixture was adjusted to pH 7.0 and was then washed with ethyl acetate. The pH of the reaction mixture was next adjusted to pH 2.5 with dilute hydrochloric acid and was then extracted with ethyl acetate containing 20% by volume of THF. The extract was dried over magnesium sulfate and was then evaporated to dryness to yield 436 mg of solid reaction product mixture.

The residue of reaction product was dissolved in 15 ml of THF and to the solution was added a solution of 400 mg of diphenyldiazomethane in 5 ml of THF. The esterification mixture was stirred for 12 hours at room temperature and was then evaporated to afford 650 mg of the crude esterified reaction product mixture.

The esterified reaction product mixture was chromatographed over preparative thin layer silica gel plates with 30% ethyl acetatebenzene to afford 116 mg of the diphenylmethyl ester of the starting material and 104 mg of the reaction product, diphenylmethyl 7-methoxy 7-[2-(2-thienyl)/acetamido]-3-(1-methyltetrazol-5-ylthiomethyl-3-cephem-4-carboxylate.

The 104 mg of esterified reaction product were dissolved in 1 ml of a cold (0° C.) mixture of equal volumes of THF and 97% formic acid and the mixture was allowed to warm to room temperature. The reaction mixture was then treated with 75 ml of methylene chloride and the solution was evaporated to dryness. The residue was dissolved in 20 ml of ethyl acetate and the solution was extracted three times with 20 ml portions of a saturated solution of sodium bicarbonate. The bicarbonate extracts were combined and were acidified to pH 2.5. The reaction product was extracted from the acidified bicarbonate extracts with 10% ethanol/ethyl acetate and the extract was dried and evaporated to yield 66 mg of the reaction product, 7-methoxy-7-[2-(2-thienyl)acetamido]-3-(1-methyltetrazol-5-ylthiomethyl)-4-carboxylic acid having the following NMR spectrum (acetone $d_6$).

220 (s, 2H, $C_2$)
266 (s, 2H, $C_3$)
305 (s, 1H, $C_6$)
209 (s, 3H, $C_7$ methoxy)
234-246 (m, 5H, amide $CH_2$, tetrazole methyl H)
421-460 (m, 5H, carboxy H, thienyl H and N-H)

I.R. (CHCl₃) 1782$^{cm-1}$ β-lactam carbonyl

EXAMPLE 17

7-Methoxy-7-mandelamido-3-(1-methyltetrazol-5-ylthiomethyl)-3-cephem-4-carboxylic acid Sodium 7-methoxy-7-mandelamido-3-acetoxymethyl-3-cephem-4-carboxylate, 1.3 mmole, prepared as described in Example 9, was dissolved in 15 ml. of water and the pH of the solution was adjusted to pH 6.5 by the addition of 0.1 N sodium hydroxide. To the solution was then added 161 mg. of 1-methyltetrazole-5-thiol and the solution was heated with stirring for 3 hours at 70° C. The reaction mixture was cooled to room temperature and to the mixture was added 50 ml of 20% THF/ethyl acetate. The pH of the mixture was adjusted to pH 2.0 with dilute hydrochloric acid and the organic layer was separated. The aqueous layer was washed twice with 20% THF/EtOAc and the organic layers were combined. The organic layers were dried over sodium sulfate and were evaporated to yield 570 mg of crude reaction product mixture.

The crude product was dissolved in 25 ml of THF and 400 mg of diphenyldiazomethane were added to the solution. The esterification mixture was stirred at room temperature for two hours and was then evaporated to dryness. The residue was leeched with a chloroform-petroleum ether mixture. The solvents were evaporated to yield 703 mg of esterified reaction product mixture.

The esterified mixture was chromatographed on preparative thin layer silica gel plates using ethyl acetate:-benzene (50:50) to provide 120 mg of diphenylmethyl 7-methoxy-7-mandelamido-3-(1-methyltetrazol-5-ylthiomethyl)-3-cephem-4-carboxylate.

The ester, 100 mg. was dissolved in 1 ml of a 50:50 mixture of THF and 97% formic acid at 0° C. The mixture was allowed to warm to room temperature and was then evaporated to dryness. Ethyl acetate was added to dissolve the residue and the solution was extracted twice with a saturated solution of sodium bicarbonate. The bicarbonate extracts were combined and were then acidified with dilute hydrochloric acid to pH 2.5. The product was extracted from the acidified bicarbonate extracts with ethyl acetate. The ethyl acetate was dried and evaporated to yield 53 mg of product, 7-methoxy-7-mandelamido-3-(1-methyltetrazole-5-ylthiomethyl)-3-cephem-4-carboxylic acid having the following NMR spectrum (60 megacycles run in acetone d₆)

218 (g, 2H, C₂)
265 (g, 2H, C₃ methylene)
305 (s, 1H, C₆)
205 (s, 3H, C₇ methoxy)
432-455 (m, 6H, phenyl and N-H)
310-317 (m, 2H, OH, and amide methine)
240 (s, 3H, tetrazole methyl).

EXAMPLE 18

To a 25 ml of tetrahydrofuran maintained at 0° C. was added 2 ml of a 1.81 molar solution of methyl lithium in ether and 4 ml of methanol. The solution was cooled to −80° C. in a dry ice-acetone bath and 700 mg of diphenylmethyl 7-[2-(1-ethoxyethoxy)-2-phenylacetamido]-3-(1-methyltetrazol-2-ylthiomethyl)-3-cephem-4-carboxylate were added. Next, .155 ml of t-butyl hypochlorite were added and the reaction mixture was stirred for 15 minutes. Glacial acetic acid, 4 ml, was added and the reaction mixture was evaporated to dryness. The reaction product was isolated from the residual reaction product mixture according to the work-up procedures described in previous examples to provide 209 mg of benzhydryl 3-methoxy-7-[2-(1-ethoxyethoxy)-2-phenylacetamido]-3-(1-methyltetrazol-2-ylthiomethyl)-3-cephem-4-carboxylate represented by the following formula.

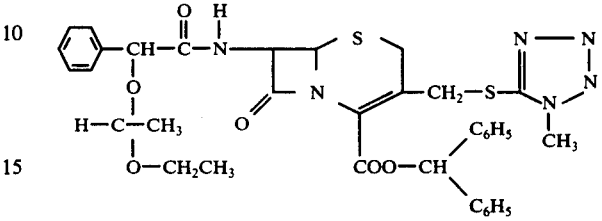

The reaction product was dissolved in 2 ml of a 50:50 mixture of TFA and 97% formic acid at 0° C. The solution was allowed to warm to room temperature and was then evaporated to dryness. The residue was dissolved in ethyl acetate and the solution was extracted with a saturated solution of sodium bicarbonate. The bicarbonate extract was acidified to pH 2.5 with hydrochloric acid and the product was extracted with ethyl acetate. The ethyl acetate extract was dried and was evaporated to dryness to yield 7-methoxy-7-mandelamido-3-(1-methyltetrazol-5-ylthiomethyl)-3-cephem-4-carboxylic acid having the same NMR and IR spectrum as the product obtained by the method described in Example 17.

EXAMPLE 19

To 25 ml of tetrahydrofuran was added 2 ml of a 1.8 molar solution of methyl lithium in ether. The solution was cooled to 0° C. and 4 ml of methanol were added to the solution. The solution was then cooled to −80° C and 468 mg of acetoxymethyl 7-[2-(2-thienyl)acetamido]-3-acetoxymethyl-3-cephem-4-carboxylate were added, followed by the addition of 0.143 ml of t-butylhypochlorite. The cold reaction mixture was stirred for 25 minutes and was thereafter diluted with 4 ml of glacial acetic acid. The acidified reaction mixture was evaporated to dryness and the residual reaction product mixture was dissolved in dichloromethane. The solution was washed consecutively with a saturated solution of sodium chloride, a dilute solution of sodium thiosulfate, a saturated solution of sodium bicarbonate, and finally with a saturated solution of sodium chloride. The washed solution was dried and was then evaporated to dryness. The residue was chromatographed on preparative thin layer silica gel plates using benzene-ethyl acetate (7:3). The location of separated materials on the chromatogram was determined with an ultraviolet lamp. The reaction product was eluted from the silica gel with acetone. The acetone was evaporated to yield 202 mg of acetoxymethyl 7-methoxy-7-[2-(2-thienyl)acetamido]-3-acetoxymethyl-3-cephem-4-carboxylate.

I claim:

1. The process for preparing a substituted β-lactam compound of the formula

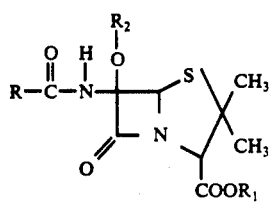

which comprises a) reacting in an inert, anhydrous solvent at a temperature between −90° and −15° C. a β-lactam ester of the formula

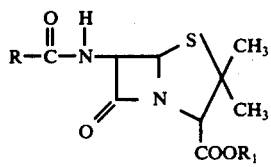

with between 2 and 6 equivalents per 1 equivalent of β-lactam ester of an alkali metal salt of the formula

in the presence of an excess of the corresponding alcohol of the formula $HOR_2$; b) adding between 1 and 5 equivalents of a halogenating agent; c) acidifying said mixture; and d) recovering the substituted β-lactam ester from the reaction mixture; where in the preceding formulae R is hydrogen, $C_1$–$C_6$ alkyl, 4-amino-4-carboxybutyl, phenyl, substituted phenyl, or a group of the formula

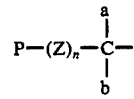

wherein
P is phenyl, $C_1$–$C_4$ lower alkylphenyl, halophenyl, hydroxyphenyl, $C_1$–$C_4$ lower alkoxyphenyl, 2-thienyl, 3-thienyl,
2-furyl, 3-furyl, or 1-tetrazyl;
Z is an oxygen atom, or a sulfur atom;
n is 0 or 1;
a is hydrogen or $C_1$–$C_3$ lower alkyl,
b is hydrogen, $C_1$–$C_3$ lower alkyl, protected hydroxy, amino, or protected amino;
and when n is 1, P is phenyl, $C_1$–$C_4$ lower alkylphenyl, halophenyl, hydroxyphenyl, $C_1$–$C_4$ lower alkoxyphenyl and
b is hydrogen or $C_1$–$C_3$ lower alkyl;
$R_1$ is hydrogen, an alkali metal cation or a readily removable ester forming moiety; and
$R_2$ is $C_1$–$C_4$ lower alkyl, allyl, propargyl, $C_3$–$C_6$ cycloalkyl, or benzyl.

2. The process of claim 1 wherein the chlorinating agent is t-butyl hypochlorite.

3. The process of claim 1 wherein $R_2$ is $C_1$–$C_4$ lower alkoxy.

* * * * *

UNITED STATES PATENT AND TRADEMARK OFFICE
CERTIFICATE OF CORRECTION

PATENT NO. : 4,044,000

DATED : August 23, 1977

INVENTOR(S) : Gary A. Koppel

It is certified that error appears in the above-identified patent and that said Letters Patent are hereby corrected as shown below:

Column 6, line 40, "propargloxycephalosporanic" should read -- propargyloxycephalosporanic --.

Column 9, line 22, "M+OR$_2$-" should read -- M$^+$OR$_2^-$ --; line 68, "employed to" should read -- employed be --.

Column 10, line 4, "M+OR$_2$-" should read -- M$^+$OR$_2^-$ --.

Column 11, line 34, that part of the structural formula reading "M$^+$OR$_2$ - R$_2$OH" should read -- M$^+$OR$_2^-$  R$_2$OH --.

Column 14, line 1, "C$_1$-C$_4$ alkyl metal alkoxide" should read -- C$_1$-C$_4$ alkyl alkali metal alkoxide --; line 37, "object" should read -- aspect --; line 62, "an" should read -- and --; line 64, "3-carbamoyl-" should read -- 3-carbamoyloxy- --.

Column 15, line 24, "of" should read -- or --; line 27, "Illustrated" should read -- Illustrative --; line 66, "gathering" should read -- generating --.

Column 18, line 65, "391 (S, 2H," should read -- 391 (s, 2H, --.

Column 21, line 40, "layer" should read -- layers --.

Column 22, line 17, "N.R.R." should read -- N.M.R. --; line 40, "which ws" should read -- which was --; line 19, "261 (s, IR, C$_3$)" should read -- 261 (s, IH, C$_3$) --.

Column 23, line 58, "of" should read -- or --; line 65, "yacetammido)" should read -- yacetamido) --.

Column 24, line 7, "propoxie" should read -- propoxide --; line 10, "3N" should read -- 3-N --.

UNITED STATES PATENT AND TRADEMARK OFFICE
CERTIFICATE OF CORRECTION

PATENT NO. : 4,044,000

DATED : August 23, 1977

INVENTOR(S) : Gary A. Koppel

It is certified that error appears in the above-identified patent and that said Letters Patent are hereby corrected as shown below:

Column 25, line 26, "in 1" should read -- in 10 --; line 29, "10" should read -- 270 --.

Signed and Sealed this

Twenty-fourth Day of October 1978

[SEAL]

Attest:

RUTH C. MASON
*Attesting Officer*

DONALD W. BANNER
*Commissioner of Patents and Trademarks*